United States Patent
Svanberg et al.

(10) Patent No.: US 8,190,240 B2
(45) Date of Patent: May 29, 2012

(54) HUMAN CAVITY GAS MEASUREMENT DEVICE AND METHOD

(75) Inventors: Sune Svanberg, Lund (SE); Linda Person, Lund (SE); Katarina Svanberg, Lund (SE)

(73) Assignee: GasPorOx AB, Dalby (SE)

(*) Notice: Subject to any disclaimer, the term of this patent is extended or adjusted under 35 U.S.C. 154(b) by 928 days.

(21) Appl. No.: 11/909,971

(22) PCT Filed: Apr. 18, 2006

(86) PCT No.: PCT/SE2006/050077
§ 371 (c)(1),
(2), (4) Date: Jun. 13, 2008

(87) PCT Pub. No.: WO2006/112789
PCT Pub. Date: Oct. 26, 2006

(65) Prior Publication Data
US 2009/0118646 A1    May 7, 2009

Related U.S. Application Data

(60) Provisional application No. 60/672,729, filed on Apr. 19, 2005.

(30) Foreign Application Priority Data

Apr. 18, 2005 (SE) .................................... 0500878-4

(51) Int. Cl.
*A61B 5/00* (2006.01)
*G01J 3/00* (2006.01)
*G01J 3/42* (2006.01)
*G01J 3/433* (2006.01)

(52) U.S. Cl. ............... 600/473; 600/407; 250/339.11; 250/339.12; 250/339.13; 250/341.8; 356/432; 356/437

(58) Field of Classification Search .................. None
See application file for complete search history.

(56) References Cited

U.S. PATENT DOCUMENTS

| | | | |
|---|---|---|---|
| 3,674,008 A | | 7/1972 | Johnson |
| 5,706,821 A | * | 1/1998 | Matcher et al. ............ 600/310 |
| 5,772,598 A | | 6/1998 | Halling |

(Continued)

FOREIGN PATENT DOCUMENTS

| | | |
|---|---|---|
| EP | 0 801 297 A1 | 10/1997 |
| EP | 1 447 044 A1 | 8/2004 |

OTHER PUBLICATIONS

United States Patent and Trademark Office, Office Action mailed Mar. 10, 2011 in U.S. Appl. No. 10/979,082, 10 pages.

(Continued)

*Primary Examiner* — Long V. Le
*Assistant Examiner* — Farshad Negarestan
(74) *Attorney, Agent, or Firm* — Inskeep IP Group, Inc.

(57) ABSTRACT

A device and method for gas measurements in body cavities are provided. These may be any body cavity containing a free gas, where there is an interest in detecting and/or measuring the concentration of said free gas by non-invasive or minimally invasive method. According to an exemplary embodiment measurement of free oxygen in cranium cavities is performed by scattering media absorption spectroscopy, and in particular variations of such oxygen. This is particularly useful for diagnostic purposes based on the measurements, for instance for detecting sinusitis or the like.

54 Claims, 8 Drawing Sheets

U.S. PATENT DOCUMENTS

| | | | | |
|---|---|---|---|---|
| 5,823,043 A | * | 10/1998 | Loucks et al. | 73/1.01 |
| 6,030,360 A | * | 2/2000 | Biggs | 604/95.01 |
| 6,646,727 B2 | * | 11/2003 | Saleh et al. | 356/73.1 |
| 7,063,667 B1 | * | 6/2006 | Ben-Oren et al. | 600/532 |
| 2003/0216617 A1 | * | 11/2003 | Hirakui et al. | 600/159 |
| 2003/0229276 A1 | * | 12/2003 | Sarussi et al. | 600/322 |
| 2004/0039269 A1 | | 2/2004 | Ward et al. | |

OTHER PUBLICATIONS

United States Patent and Trademark Office, Final Office Action mailed Aug. 11, 2010 in U.S. Appl. No. 10/979,082, 7 pages.

United States Patent and Trademark Office, Office Action mailed May 7, 2010 in U.S. Appl. No. 10/979,082, 6 pages.

WIPO, U.S. International Search Authority, International Search Report mailed Jul. 15, 2003 in International Patent Application No. PCT/SE03/00717, 2 pages.

Sjöholm, M. et al., "Analysis of gas dispersed in scattering media," *Optics Letters,* vol. 26, No. 1 Optical Society of America, Jan. 1, 2001, 3 pages.

Seltman. J., "Indication of slope-of-gain and biodegradation in wood with electromagnetic waves," *Seminar/Workshop on Scanning Technology and Image Processing on Wood,* Skelleftea, Sweden, Sep. 1, 1992, 16 pages.

\* cited by examiner

HUMAN CAVITY GAS MEASUREMENT DEVICE AND METHOD

RELATED APPLICATIONS

This application claims priority to International Application No. PCT/SE2006/050077, International Filing Date Apr. 18, 2006, entitled Human Cavity Gas Measurement Device And Method, which claims priority to Swedish Application No. 0500878-4 filed Apr. 18, 2005 entitled Mätmetod Och Anordning För Gasmätning I Människans Hälrum, and U.S. Provisional Application No. 60/672,729 filed Apr. 19, 2005, entitled Human Cavity Gas Measurement Method And Device, all of which are hereby incorporated by reference.

FIELD OF THE INVENTION

This invention pertains in general to the field of gas measurements in cavities. More particularly the invention relates to a device and method for measuring free, i.e. unbound gas in human cavities.

BACKGROUND OF THE INVENTION

There is an interest in detecting inflammations in the human body without invasively inspecting the body.

Most known methods and devices are complicated and expensive.

Hence, an improved device and method would be advantageous and in particular allowing for increased flexibility, cost-effectiveness, non-invasiveness and user friendliness would be advantageous.

WO 03/093803, and corresponding U.S. Ser. No. 10/979,082 of same applicant disclose a method and device for investigation of a surface layer (e.g. paint) of a material, wherein a penetration of a gas into the material through the surface layer is measured. The measurement of the passage of said gas into the material is performed by a method comprising measurement of light absorption by said gas by absorption spectroscopy. However, this method and device are not provided for medical purposes according to the disclosure. U.S. Ser. No. 10/979,082 is herein incorporated by reference in its entirety.

U.S. Pat. No. 3,674,008 discloses an instrument which quantitatively measures optical density of the transilluminated body portion. The instrument comprises a controllable, relatively low-frequency oscillator generating pulses which are applied to a light source through a first expand and delay circuit. A light conducting means, optically couples the light source to one side of the body portion and a similar means optically couples another side of the body portion to a light detector. After compensation for ambient light, the output of the detector is coupled to a sample and a hold circuit that is triggered by the controllable oscillator through a second expand and delay circuit. The stored signal in the sample and hold signal is proportional to transmittance and is converted to a visual indication of optical density by a calibrated display means. However, U.S. Pat. No. 3,674,008 fails to disclose the measurement of free gas in body cavities, since the instrument only relies on the fact that fluids lead light better than opaque material, thus being able to detect light travelling in fluid light conducting paths.

U.S. Pat. No. 5,706,821 discloses a spectrometric technique for quantitatively determining the change in concentration of a substance which is contained in a medium which both absorbs and scatters spectroscopically interrogated radiation. The medium includes a plurality of such regions displaying potentially different absorption and scattering properties to the radiation. Specific applications are disclosed involving the noninvasive determination of changes in concentration of the substances oxyhemoglobin and deoxyhemoglobin and/or changes in the redox state of the substance cytochrome oxidase within the brain or skeletal muscle. However, U.S. Pat. No. 5,706,821 fails to disclose the change of concentration of an unbound gas by measuring the gas in itself. The only technique for quantitatively determining the change in concentration is through an intermediate, i.e. oxyhemoglobin and/or deoxyhemoglobin.

EP 0801297 discloses a method of projecting measuring light to a measurement portion of an object with high reproducibility so as to always establish a constant measuring condition. An optical measuring apparatus is disclosed in EP 0801297 that includes a spectral analysis portion for detecting a spectral intensity of reflected light of measuring light projected to the hand of a subject. When the measurement portion of the hand is registered, an image of the palm of the hand is taken by a CCD camera, and an operator selects a portion having characteristics features from the pattern of the image so taken. When spectral analysis is executed, the palm of the hand is again imaged by the CCD camera, the portion at the time of registration is detected from the pattern of that image, and after the spectral analysis portion is moved by a movement mechanism, and measuring light is allowed to be incident on the characteristic feature portion so registered. However, EP 0801297 fails to disclose the measurement of free gas in body cavities.

OBJECTS AND SUMMARY OF THE INVENTION

Accordingly, the present invention preferably seeks to mitigate, alleviate or eliminate one or more of the above-identified deficiencies in the art and disadvantages singly or in any combination and solves at least partly the above-mentioned problems by providing a device, and a method, according to the appended patent claims.

The general solution is based on the measurement of a free gas in a body cavity.

According to a first aspect of the invention, a device is provided, wherein the device is adapted to perform the method according to a further aspect of the invention described below.

More precisely, according to an embodiment, a device configured to measure free gas in a body cavity is provided. The device comprises a light emitter configured to emit light towards said body cavity from outside said body cavity, and a light receiver configured to collect scattered light from tissue surrounding said body cavity, configured to observe at least one wavelength window specific for a free gas in the body cavity; and a calculating means for assessing a concentration of said free gas in said body cavity from said collected scattered light, based on optical absorption spectroscopy.

The receiver may be arranged outside the body.

The wavelength window specific for a free gas is according to an embodiment approximately $1/10000$ of that of bound molecules.

The calculating means may be configured to calculate a concentration ratio between a reference gas and said free gas, to thereby determine the concentration of said free gas. The reference gas concentration may be a known concentration of free water vapour, such as the water vapour concentration in the lungs other body cavities, and said ratio of water vapour to the unknown gas is determinable by said calculation means, as proportional to the concentration of free oxygen or free carbon dioxide.

The light emitter may be comprised in an endoscope or a fiberoptic catheter.

The device may be in a compact, handheld configuration, adapted to be applied to the outside of said body for measuring said free gas in said body cavity.

The light emitter may be a near-IR single mode diode laser.

The light receiver may be a photomultiplier tube.

The gas may be selected from the group comprising oxygen, methane, carbon dioxide, water vapour, or nitric oxide.

The device may be configured to perform said optical absorption spectroscopy in scattering media in transmission or backscattering.

The light emitter and light receiver may be arranged in a transmission geometry or in a backscattering geometry.

The light receiver may be configured to transform said collected scattered light to a signal. The device may comprise means for splitting said signal into a first signal and a second signal. The device may be configured to send said first signal to a computer controlled digital oscilloscope, and said second signal to a lock-in amplifier. The device may be configured to send said second signal thereafter to said oscilloscope.

The device may comprise said light emitter and said light receiver (4) in a measurement head directly positionable onto the skin of a subject.

The device may be configured to provide dynamic measurements of said free gas.

The device may be configured for diagnostic purposes, such as for detecting physiological processes or physiological anomalies or diseases or in subjects. The physiological processes may be respiration of a subject. The physiological anomalies or diseases may comprise inflammations or infections.

The free gas may be nitric oxide (NO) and said device may be configured to determine a level of infection from said detected free NO.

The device may be configured for diagnosing sinusitis, pleural infections, gastro-intestinal diseases, or ear-infections in subjects.

The device may be configured for neonatal subjects, having said body cavity.

According to another aspect of the invention, a method is provided for this purpose.

More precisely, a method of non-invasively measuring free gas in a body cavity is provided. The method comprises emitting light towards said body cavity from outside said body cavity, collecting scattered light from tissue surrounding said body cavity, in order to thereby observe at least one wavelength window specific for a free gas in the body cavity; and assessing a concentration of said free gas in said body cavity from said collected scattered light, based on the technique of optical absorption spectroscopy.

The method of measuring of said gas in said body cavity may be a method comprising absorption spectroscopy measurement of said gas in scattering media. The measurement may be performed in transmission or backscattering.

The wavelength window specific for a free gas is approximately ¹/₁₀₀₀₀ of that of bound molecules.

The assessing may comprise calculating a concentration ratio between a reference gas and said free gas, to thereby determine the concentration of said free gas.

The concentration of said reference gas may be a known concentration of free water vapour, such as the water vapour concentration in the lungs other body cavities, and said ratio of water vapour to the unknown gas may be used to determine, the concentration of free oxygen or free carbon dioxide.

When said concentration of free water vapour is 100% said ratio is directly proportional to said concentration of said free gas.

Said emitting and collecting may be achieved through transmission geometry or through backscattering geometry.

The method may comprise transforming said collected scattered light to a signal.

The method may comprising splitting said signal into a first signal and a second signal.

The method may comprise sending said first signal to a computer controlled digital oscilloscope, and sending said second signal to a lock-in amplifier.

The method may comprise sending said second signal thereafter to said oscilloscope.

The method may comprise comprising introducing light for scattering media absorption spectroscopy into the body by means of a light guide, such as a fiberoptic catheter or endoscope for analysing deeper lying body regions for free gas containing cavities.

The method may comprise introducing light for scattering media absorption spectroscopy into the body cavities inside the body from the outside of the body.

The method may comprise placing a measurement head directly onto the skin of a subject.

The method may comprise providing dynamic measurements of said free gas.

According to a further aspect of the invention the method according to the above aspect of the invention is used for diagnosing diseases based on the measurements of free gas in body cavities.

More specifically, said free gas measurement method in body cavities is used for diagnostic purposes, such as for detecting physiological processes or physiological anomalies or diseases or in subjects.

The physiological processes may be respiration of a subject.

The physiological anomalies or diseases may comprise inflammations or infections.

The free gas may be nitric oxide (NO) and a level of detected free NO may be used to determine a level of infection.

The use may be diagnosing sinusitis, pleural infections, gastrointestinal diseases, or ear-infections in subjects.

The use may be performed with neonatal subjects, having said body cavities.

The present invention thus provides an advantageous device and method. The device may be conveniently integrated into a handheld form in order to non-invasively measure conditions inside the human body.

BRIEF DESCRIPTION OF THE DRAWINGS

These and other aspects, features and advantages of which the invention is at least partly capable of will be apparent and elucidated from the following description of embodiments of the present invention, reference being made to the accompanying drawings, in which.

DETAILED DESCRIPTION OF THE INVENTION

The following description focuses on an exemplary embodiment of the present invention applicable to a method and device configured for measurement of free oxygen in cranium cavities, and in particular to variations of such oxygen, preferably for diagnostic purposes thereof. However, it will be appreciated that the invention is not limited to this application but may be applied to many other body cavities containing a free gas, wherein there is an interest in detecting and/or measuring the concentration of said gas by means of using a non-invasive method or device.

Figure 2:
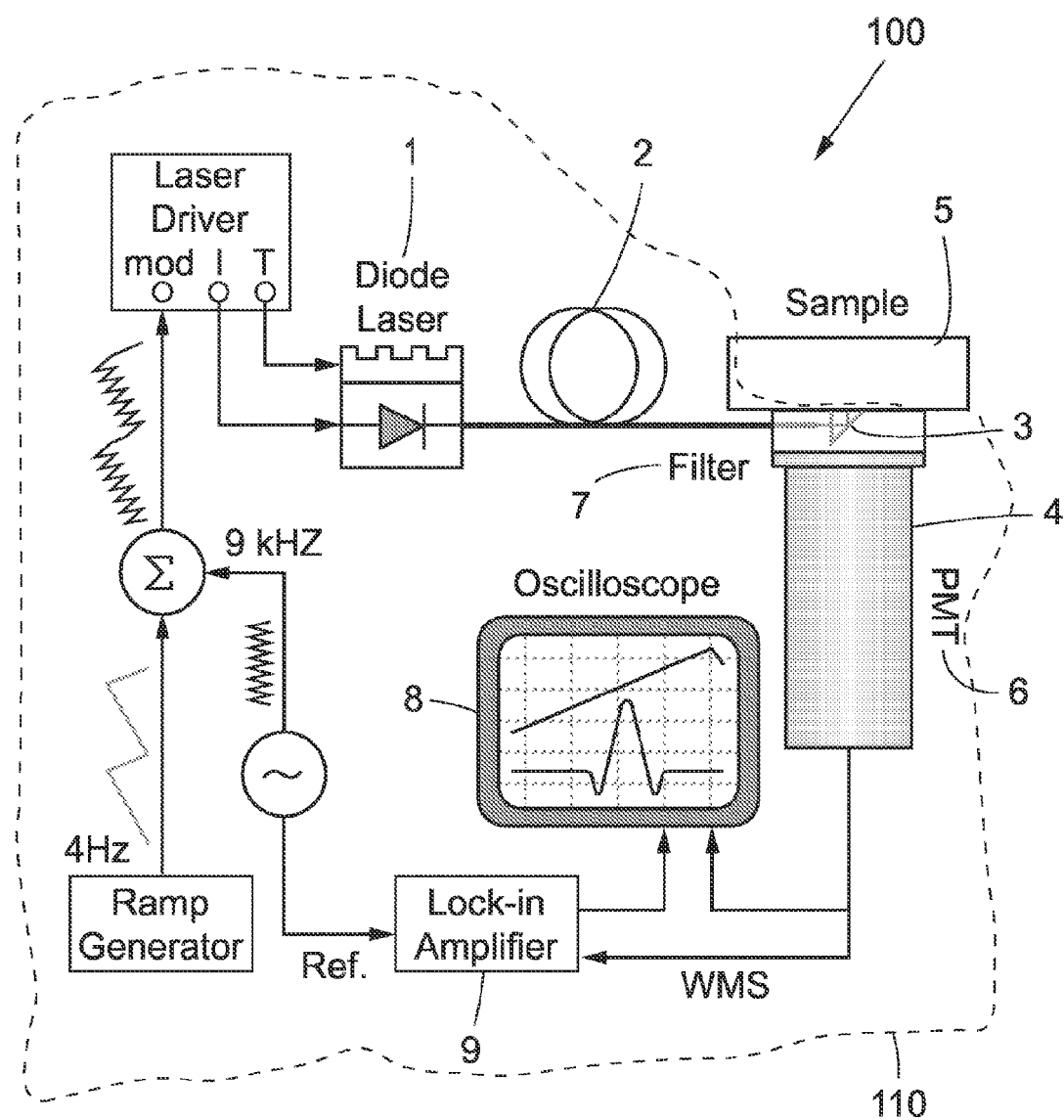
FIG. 2 is a schematic diagram showing the experimental arrangement and an embodiment of the apparatus according to the invention.

In an embodiment of the apparatus of the present invention is given with reference to FIG. 2, using a method according to an embodiment of the present invention.

According to the embodiment, a method for measuring free oxygen gas in head cavities is provided. The method may be applied for diagnostics of a common disease, sinusitis. The measurement method is based on absorption spectroscopy on the free oxygen gas. The human sinus cavities are normally air-filled and the presence of this gas is observed by wavelength modulation spectroscopy using tuneable diode lasers.

Inflammation such as sinusitis frequently leads to liquid and pus filling the cavities thereby altering the gas content in the cavities. Also, in such clogged cavities, gas exchange is more or less hindered and dynamic gas concentration changes are influenced. This is the basis of the present embodiment, giving measurement signals related to the content of free molecular gas in the cavities. Hereinafter, it is demonstrated how the molecular oxygen signal around 7 60 nm is observed through the external facial tissue as light is backscattered from deeper lying structures through the gas filled cavity.

According to alternative embodiments, a transmission geometry is provided for the maxillary sinuses using fibreoptic light injection from the oral cavity, as well as cheek monitoring.

The sinus gas signal may be studied statically, but also dynamically, by observing the presence or absence of gas transport through open or occluded nasal channels, respectively. In such measurements, a gas of non-ambient oxygen composition is used such as air exhaled from the lungs.

Human tissue exhibits a comparatively low absorption in the range 600-1400 nm (tissue optical window), where scattering, however, is strongly dominant. Optical transillumination in this wavelength interval is being investigated for optical mammography. The technique presented in the present paper utilizes experience gained in gas in scattering media absorption spectroscopy (GASMAS), where, however, gas distributed throughout the scattering medium is studied. Such distributed gas gives rise to a very sharp (e.g. 0.001 nm) absorptive imprint in contrast to the broad structures due to molecules in liquids or solids. This means that a wavelength window specific for a free gas is approximately $1/10000$ of that of bound molecules. According to the present embodiment, light passes through a macroscopic gas cavity mediated through diffusely scattering "mirrors", wherein the cavity status according to an embodiment is assessed from a measurement head pressed towards the facial tissue. The use of absorption spectroscopy for this purpose allows providing a measurement signal associated with the concentration of free gas in a body cavity from outside the body cavity. The spectroscopy is based on the principle that a very narrow wavelength window is used where tissue, which is surrounding a cavity filled with free gas, scatters has an absorption coefficient at the wavelength used that is negligible compared to its scattering coefficient. On the contrary, a free gas of interest has at this very narrow wavelength scattering coefficient at the wavelength used that is negligible compared to its absorption coefficient. Hence, when absorption spectroscopy is used, a measurement signal is provided which is associated with the concentration of the free gas in the cavity, as this mainly determines the grade of absorption, and not the surrounding tissue. Such a wavelength is for instance for free molecular oxygen around 7 60 nm and for free water vapour around 980 nm. Moreover, a line width used for the measurements of diffuse transmission or backscattering is according to embodiments for instance in the range of 0.01 to 0.0001 nm.

Facial Anatomic Background

Figure 1:
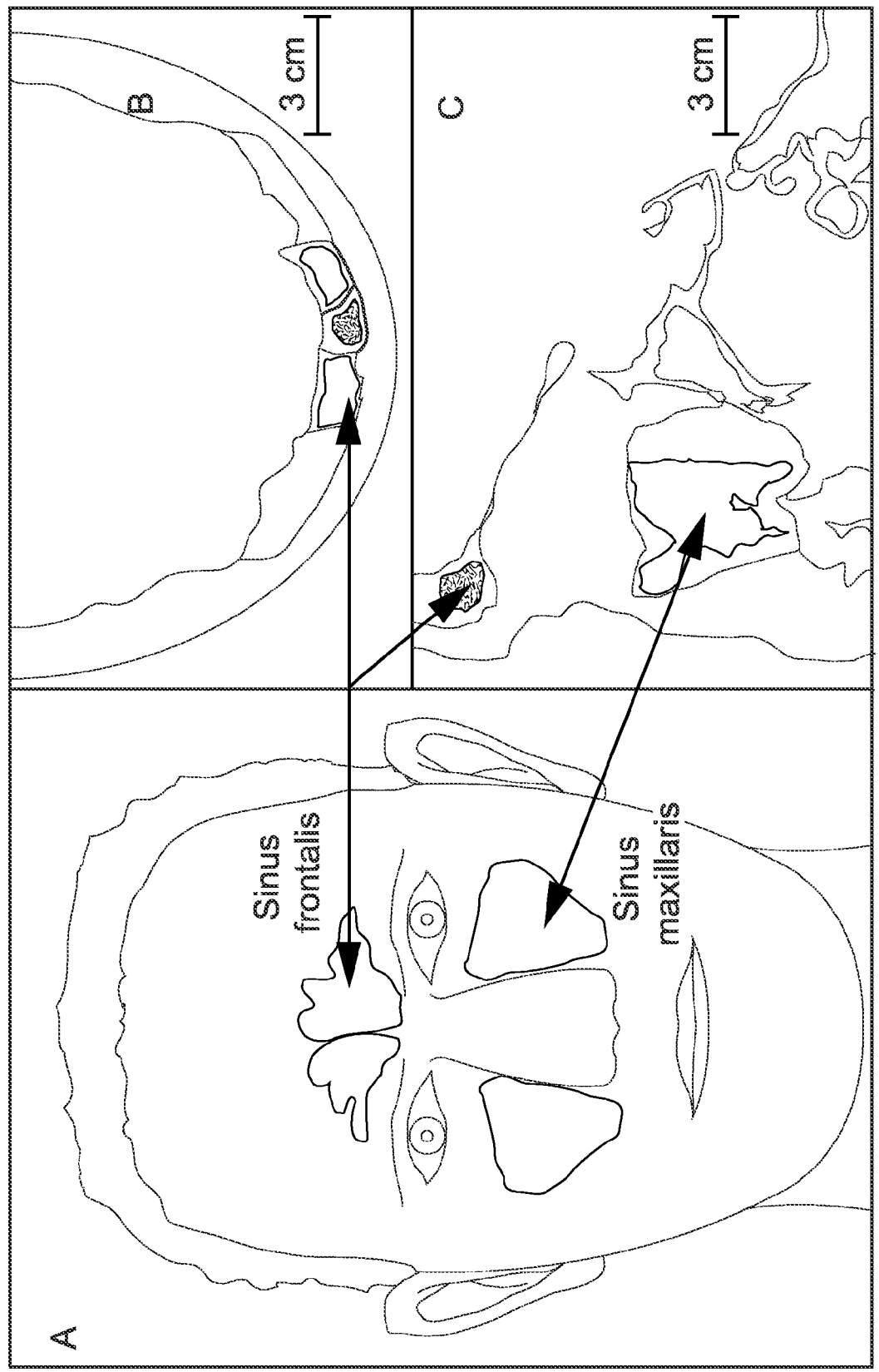
FIG. 1A is an illustration showing the location of the frontal and maxillary sinus.
FIG. 1B is a CT image of a human frontal sinus, horizontal section.
FIG. 1C is a CT image of the frontal and maxillary sinuses, vertical section.

The facial skeleton in the nasopharyngeal areas features several cavities, also called sinuses, as illustrated in FIG. 1. The frontal sinus most often consists of one single cavity but can sometimes have different compartments. The maxillary and sphenodial sinuses are bilateral. The ethmoidal cellular system is also bilateral and consists of many smaller communication cavities. The frontal sinus is located in the frontal bone of the skull just above the eye bulbs. The maxillary sinuses are located on each side in the maxillary part of the cheek just below the orbital floor. The ethmoidal cells and the spheodal sinus, which is not shown in FIG. 1, are located in the medial and dorsal part of the nose. All sinuses are connected to the nose cavity for drainage, at least for healthy subjects.

Sinus Inflammation and Diagnostics

Inflammation of the nasal accessory sinuses is most often related to viral infections in the area or to allergic reactions. This usually causes a swelling of the mucosal tissue, resulting in an occlusion of the drainage passage. In these closed cavities, bacteria will grow and cause clinical manifestations, called sinusitis. The diagnosis of sinusitis is based on the anamnestic history of the patient along with clinical investigations, such as cheek palpation and visual inspection with a speculum for purulent fluid of the nasal cavity. Paraclinical investigations include sinus X-ray, ultrasound and low dose computerized tomography. Among these methods, ultrasound and sinus x-ray investigations are seldom used these days. Assessing the sinus status is sometimes not straightforward, and a simple tool for additional diagnostics would be welcome. A powerful diagnostic modality might lead to a reduction in unnecessary antibiotic treatment. Such a modality is provided by embodiments of the present invention.

According to the present embodiment, an optical technique based on absorption laser spectroscopy is provided for investigating the condition of the sinuses. The location of both the frontal and the maxillary sinuses is well suited for optical investigations from the outer part of the face. The frontal sinus is separated by a bone and tissue structure of approximately 10 mm and the cavity has a thickness of typically 10 mm. The maxillary sinuses are located behind approximately the same thickness of bone and muscle tissue. The cavities exhibit a larger transverse air distance of up to 3 cm. As discussed below, this may be used for measurements in transmission, more precisely the ethmoidal cells as well as the sphenoidal sinuses, may be reached from the nasal cavity for light injection as well as detection. The former aggregation of cells can be infected (ethmoiditis), especially in children, which is considered as a particularly serious condition, given the close proximity to the orbital cavities.

Experiment

A supporting experiment related to sinusitis diagnostics based on gas spectroscopy was performed in two stages. First, a model system consisting of two air-spaced plastic scatterers was investigated in backscattering and in transmission with a number of parameters being varied. Second, measurements on the sinus cavities on a volunteer were then performed in-vivo in order to verify the in-vitro results. This is described hereinafter. Experimental set-up An embodiment of a device 110 according to the invention is given in FIG. 2. A schematic diagram of the gas detection setup is shown at 100. A near-IR single mode diode laser 1, namely a Sharp LT031 MDO with a nominal output power of 7 mW, was used as the spectroscopic light source. By applying a ramp at a repetition rate of 4 Hz to the driving current, the diode laser 1 was temperature tuned across the R7R7 molecular oxygen line, situated at 7 61.003 nm (vacuum wavelength). As can be seen on the left of FIG. 2, a 9 kHz sine-wave was superimposed onto the current ramp to produce a wavelength modulation of the light, thereby providing sensitive wavelength modulation spectroscopy (WMS).

An optical fibre 2 with a 600 urn core diameter was used to guide the light to the sample. For backscattering measurements, a small right-angle prism 3 positioned in front of the distal end of the fibre 2 and centrally located of the detector 4, was used to provide total internal reflection in order to launch the light into the sample 5, which effectively was exposed to about 2 mW. An annular aperture with an inner and an outer aperture diameter of 10 and 21 mm, respectively, was used to collect the backscattered photons from the sample 5. For a transmission geometry (not shown in FIG. 2), the fibre was positioned above the sample 5 and a circular aperture with a diameter of 5 mm was used in front of the detector (as shown in FIG. 3B). In order to achieve efficient photon collection with a high dynamic range, the light was detected with a photomultiplier tube 6, Hamamatsu 5070A, protected from visible light by a blocking colored glass filter 7, here a Schott RG715.

The absorption signal was detected by splitting up the signal from the photomultiplier tube into two parts. One part, referred to as the direct signal, was directly sent to a computer controlled digital oscilloscope 8. The other part, referred to as the WMS signal, was sent to a lock-in amplifier 9, here an EG&G Princeton Applied Research 5209, providing phase-sensitive detection at twice the modulation frequency, before sent to another channel on the oscilloscope 8, as illustrated in FIG. 2. Wavelength modulation spectroscopy with lock-in detection is often referred to as derivative spectroscopy, since the signal looks like the derivative of the absorption profile. In this case, when detection at twice the modulation frequency is done, the lock-in signal looks like the second derivative of the absorption profile.

The amplitude of the WMS signal is determined by the absolute size of the narrow gas absorption feature, i.e., the fractional absorption due to the gas and the amount of light reaching the detector. By measuring the peak-to-peak value of the absorption signature in the WMS signal and normalize it with respect to the amount of light reaching the detector (the direct signal), the absorption due to the gas of interest is estimated. For small absorptions, the WMS signal is proportional to the absorbance and thus to the product of the gas concentration and the path length traveled by the light.

A method called standard addition was adopted in order to calibrate a normalized measured WMS signal and transform it into a useful quantity. By adding known path lengths of ambient air to be traversed by the laser light in addition to the scattering object and by plotting the acquired normalized WMS values as a function of added air, we an equivalent air distance is estimated. The data points in such a plot are expected to fall on a straight line. The zero crossing yields the equivalent distance in ambient air, Leq, giving rise to a signal with the same magnitude as a signal from the sample.

Measurements

Model System Measurements

Figure 3:
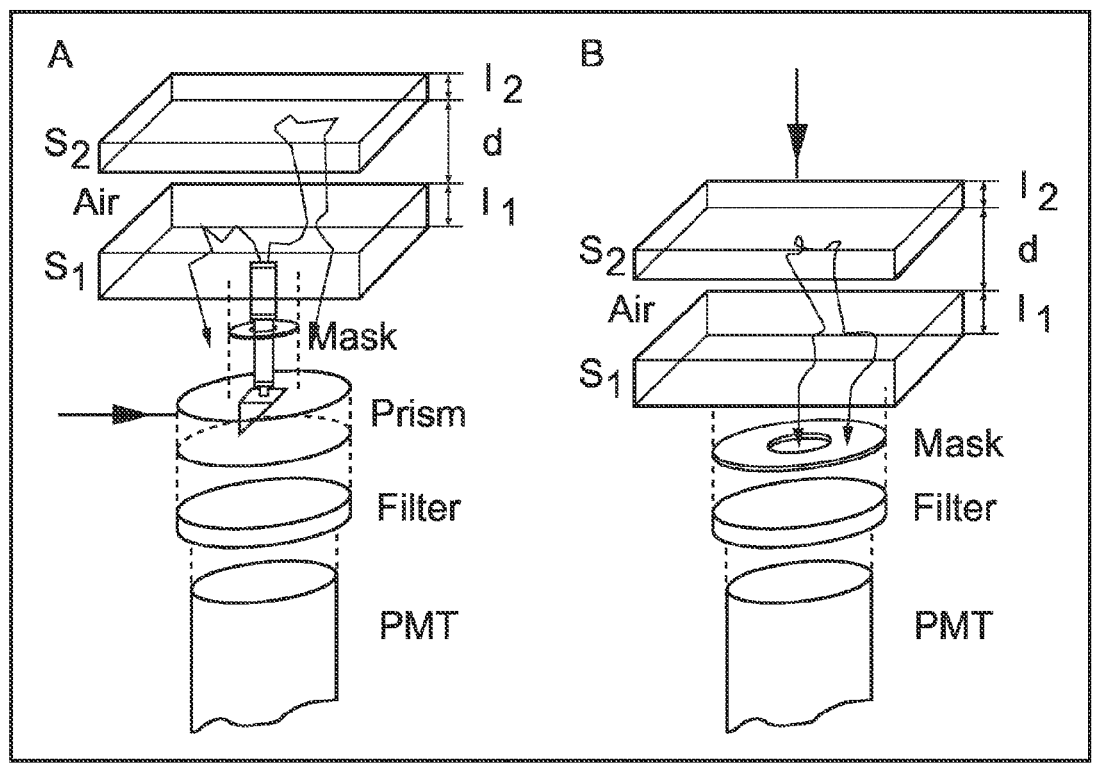
FIG. 3A illustrates the arrangement of a phantom imitating the case of measurements on the frontal sinuses in a backscattering geometry.
FIG. 3B illustrates the arrangement of a phantom imitating the case of measurements on the maxillary sinuses in a transmission geometry.

Human phantom measurements were performed on the system shown in FIG. 3. Laser light is injected into a primary scatterer $S_1$ of thickness $I_1$, separated by a distance d from a secondary scatterer $S_2$ of thickness $I_2$. The scatterers are made from Delrin plastics, which have a scattering coefficient similar to that of human tissue. As in the case of human tissue, its absorption coefficient at the wavelength used, 760 nm, is negligible compared to its scattering coefficient.

Figure 8:
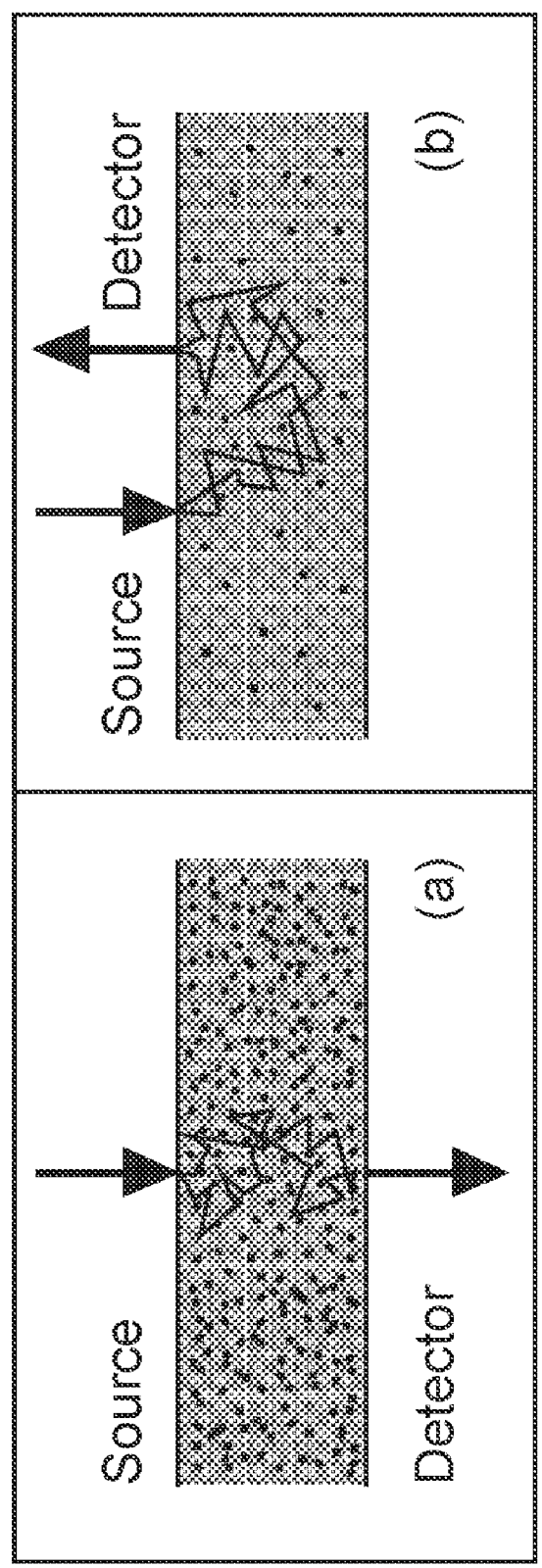
FIG. 8 is a schematic illustration of forward/transmission scattering (left of FIG. 8) and backscattering (right of FIG. 8).

In FIG. 3A, a backscattering geometry is illustrated, wherein photons injected into $S_1$ are multiply scattered internally. The principle of backscattering is also illustrated in FIG. 8 on the right. Some photons escape into the air gap separating the scatterers and cross it along straight lines before penetrating into $S_2$. Here, multiple scattering occurs and some photons cross the air gap again to be scattered again in $S_1$. A small fraction of the photons primarily injected into $S_1$ will ultimately pass this scatterer again after passing the air gap twice before being detected by the photomultiplier. Such photons have traveled an air distance longer than 2d. For a pathlength of 2d=20 mm, a fractional absorption of $4 \times 10^4$ due to the R7R7 oxygen line, is expected for air of normal ambient composition. Most of the light reaching the photomultiplier is backscattered only from $S_1$ and thus will not have a gas absorptive imprint. Therefore, the fractional absorptive signal will be diluted. Gas signal contributions from multiple passes through the air gap will be negligible. Clearly, the unwanted contribution from photons scattered in $S_1$ can only be strongly reduced by choosing a sufficiently large central beam stop before the photomultiplier cathode. This is in accordance with the normal observation that by increasing the distance between the source and the detector, deeper volumes of the scattering medium are probed.

Measurements in transmission geometry are illustrated in FIG. 3B. The main difference with the backscattering case is that all photons reaching the detector must now have crossed the air gap. However, the dominant signal contribution now comes from a single air-gap pass.

Figure 4:
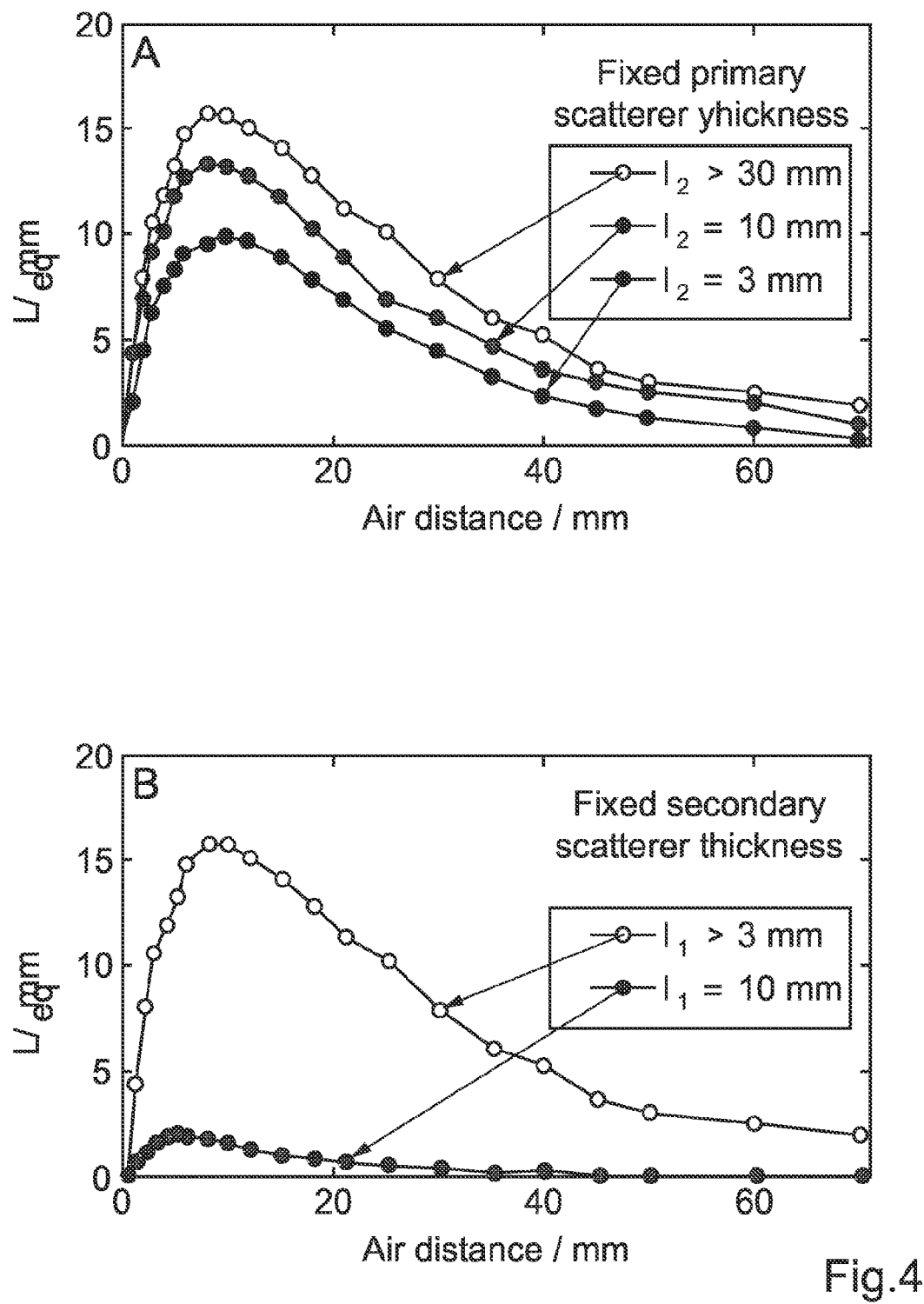
FIG. 4A shows in a schematic chart an oxygen signal as a function of cavity thickness for different secondary scatterer dimensions with a fixed primary scatterer of thickness 3 mm, measured in backscattering geometry.
FIG. 4B shows in a schematic chart an oxygen signal as a function of cavity thickness for different primary scatterer thicknesses with a fixed secondary scatterer thickness above 30 mm, measured in backscattering geometry.
Figure 5:
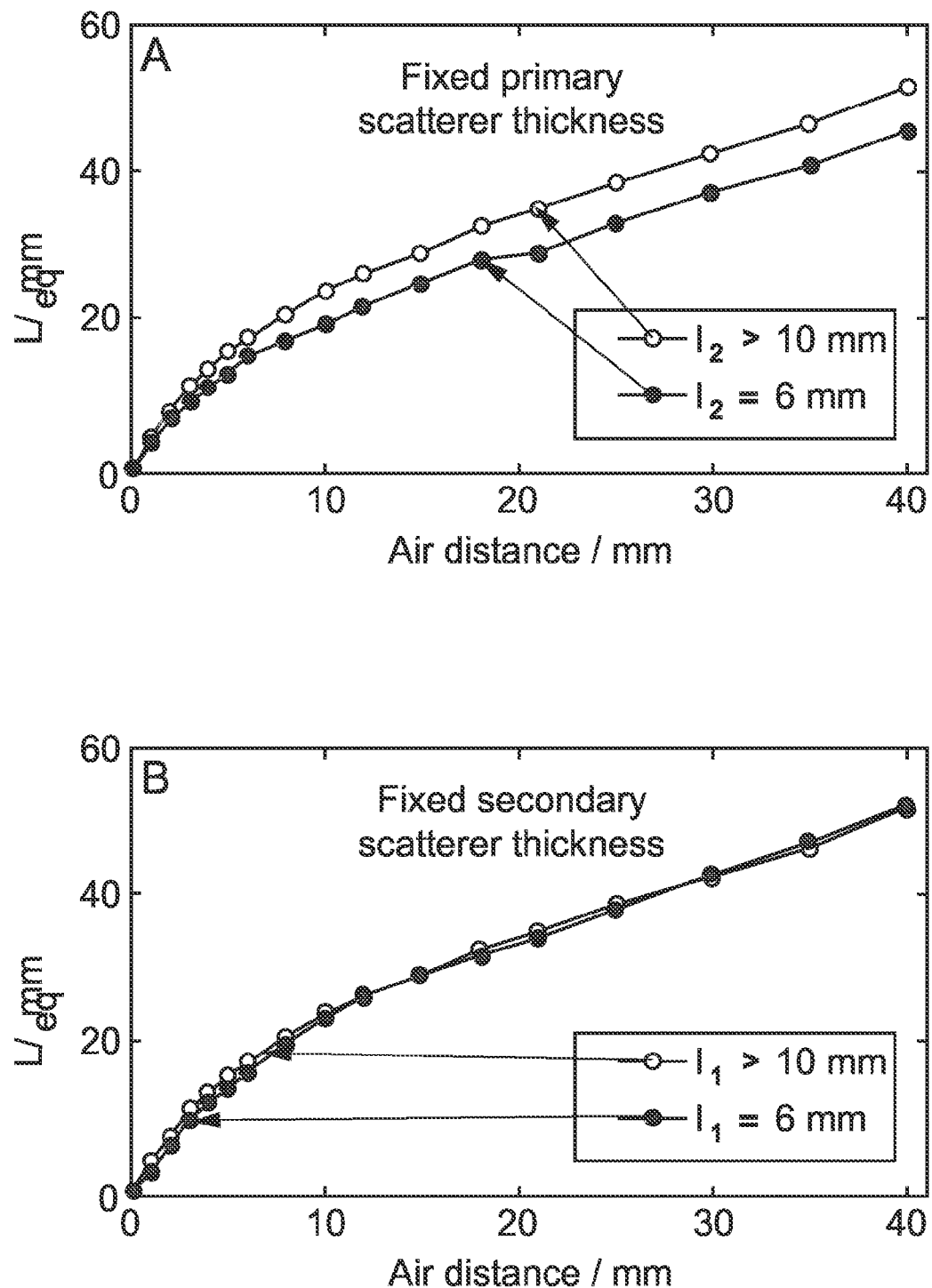
FIG. 5A shows in a schematic chart an oxygen signal as a function of cavity thickness for different secondary scatterer dimensions with a fixed primary scatterer of thickness 10 mm, measured in transmission geometry.
FIG. 5B shows in a schematic chart an oxygen signal as a function of cavity thickness for different primary scatterer dimensions with a fixed secondary scatterer of thickness 10 mm, measured in transmission geometry.

In order to study the influence of the primary and secondary scatterers in the backscattering geometry, thus emulating measurements on the frontal sinuses, a first series of measurements was performed where the oxygen signal was measured for a fixed value of $I_1$, while d and $I_2$ were varied, see FIG. 4A. In a second series of measurements, the same procedures were carried out, this time, with a fixed value of 12, while $I_1$ was varied; see FIG. 4B. From FIG. 4A, we note that the total oxygen signal increases with increasing secondary scatterer thickness. This increase, however, rapidly decays and eventually stops after a certain thickness, around 30 mm, beyond which the secondary scatterer can be considered as an infinitely thick scatterer. This case pertains to clinical measurements where bone and brain constitute the massive secondary scatterer and large variations due to the properties of this scatterer are not expected. However, as can be seen in FIG. 4B, the primary scatterer will effect the measurements to a much larger extent since different humans have different depths into the sinuses. The signal starts to fall off for air distances above a certain threshold since photons from $S_2$ are more likely to be scattered outside of the finite size detector. By the same rationale, the signal levels are lower for a thicker primary scatterer, Since the maximum oxygen signal occurs for air distances of the order of 5-10 mm, this effect is not be a limitation in human measurements on the frontal sinuses. However, for the thicker maxillary sinuses, the occurrence of the same signal for two different path lengths might cause problems. The transmission alternative pertaining to that case yielded data shown in FIG. 5, and is principally illustrated in FIG. 8 on the left thereof.

In this geometry, the thickness of the primary scatterer does not have the same impact on the oxygen signal. The oxygen signal increases with air distance, since all collected photons must have traveled through the air distance. For very large distances, however not relevant in this application, Leq is equals the actual air distance, but for small air distances the oxygen signal will be larger because of additions due to longer pathlengths at an angle, see FIG. 5A. The influence of the thickness of the secondary scatterer is negligible, see FIG. 5B.

Figure 6:
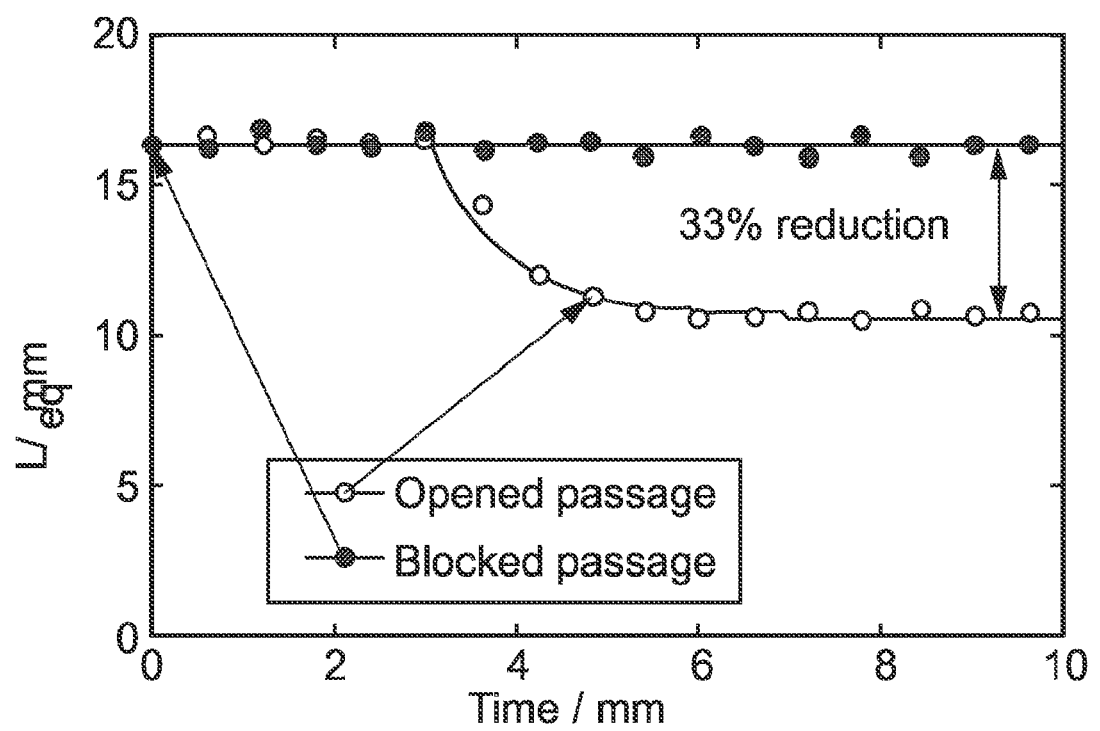
FIG. 6 shows in a schematic chart the change in oxygen signal as the gas in the phantom airspace is gradually replaced by a different gas mixture supplied by diffusion (Ii=3 mm, 12>30 mm, d=8 mm), wherein measurements were performed in backscattering geometry.

In order to simulate gas transport between a sinus cavity and the nasal cavity, the air gap was replaced with a small air filled plastic bag filling the gap. This experiment can be done in both backscattering and transmission geometries on the maxillary sinuses and in backscattering geometry on the frontal sinuses. In all cases the oxygen signal is expected to decay for the fixed geometry at hand. The bag was connected with a larger nitrogen filled bag via a valve and a plastic tube, in which cotton wool was inserted to reduce the passage. FIG. 6 shows the change in oxygen signal when the gap oxygen content is reduced through diffusion, measured in backscattering geometry with $I_1=3$ mm and $I_2=10$ mm. Specifically, no change in signal is expected when the passage is blocked, as is also shown in the figure.

Human Tests

Figure 7:
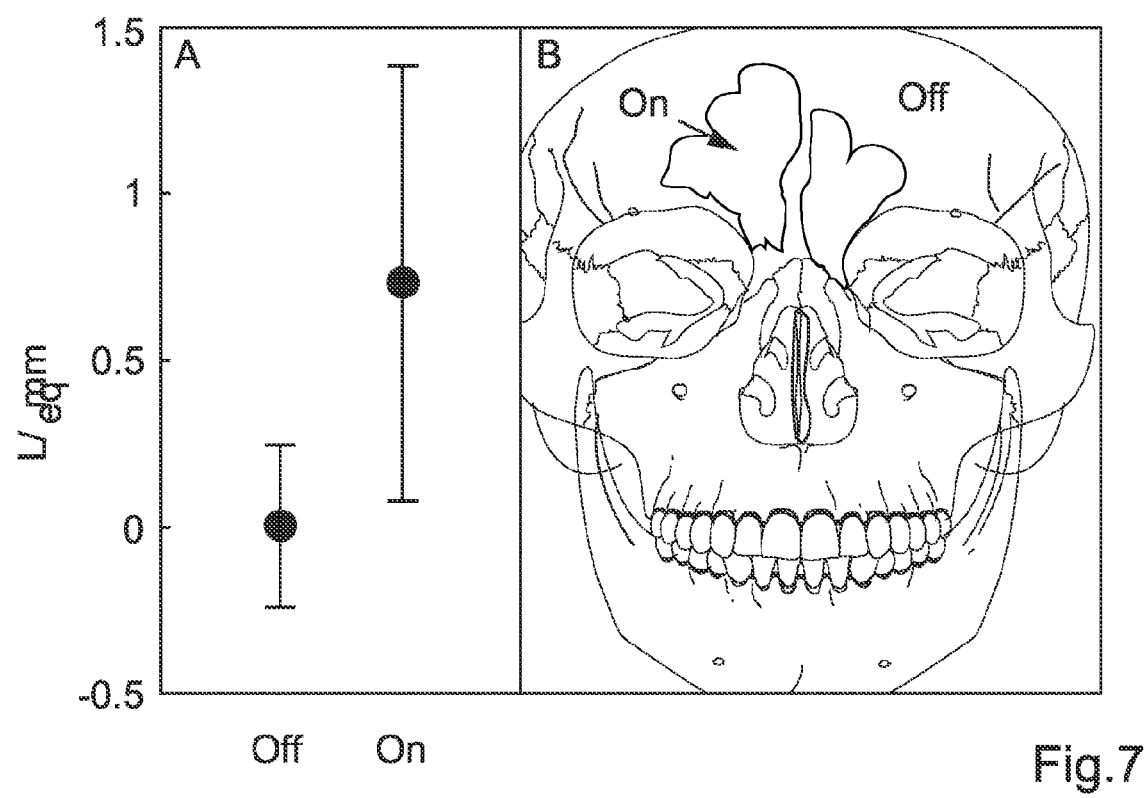
FIG. 7A illustrates the average Leq from measurements on and off the frontal sinus on a healthy volunteer, as shown in FIG. 7B, together with error bars corresponding to one standard deviation.
FIG. 7B is a schematic X-ray image on the volunteer of FIG. 7A, showing the extent of the frontal sinuses.

In order to investigate the viability of the method for real human diagnostics, signals were recorded with the measurement head against the forehead of a volunteer. Data from measurements on the frontal sinus, and at a closely-lying reference (solid tissue) location are given in FIG. 7. The average Leq on the frontal sinuses varies substantially, which is expected since the frontal sinus is not a cavity with fixed thickness, while measurements outside the frontal sinuses results in a very stable zero signal, see FIG. 7a. Consistently, it was also noted that a human underarm yielded a stable zero level. These results indicate that the present method may be used for real-time monitoring of the gas content across the frontal sinuses resulting in a low-resolution oxygen gas image. A substantially improved signal-to-noise level may be provided from an optimized set-up.

The measurements presented for the phantom and for the volunteer show that the presence of free gas in normal human sinus cavities is monitored by the above described set-up, as well as gas exchange through the connecting passages. The results suggest that anomalies due to sinus infections, with air being replaced by liquid, and a clogged passage are detectable, and that a new method for non-intrusive and real-time diagnostics is provided. For the dynamic gas measurements, the difference in oxygen content in inhaled and exhaled air, 21 and 16 percent, respectively, might be used, employing the proper breathing technique. In this way, the method presents a way of respiratory monitoring. More precisely, the change of inhaled and exhaled air in the sinuses, measured from the outside of the body, shows typical patterns for a healthy subject, namely oxygen content dropping from around 21 to 16 percent during expiration and raising back to 21 percent, when ambient air is taken in and spread through the cavities during inspiration.

A compact handheld instrument with substantial diagnostic power is provided by an embodiment of the invention, wherein components of suitable small size of the above-described device are used.

Other embodiments may include and provide measurements on other physiological gases such as carbon dioxide, water vapour or methane with overtone absorption bands in the tissue optical window. In particular, measurements of concentration ratios are independent of the scattering properties and may supply valuable diagnostic information for occluded sinus cavities. Dynamic measurements might also be advantageous due to the higher contrast provided by using carbon dioxide, for which the concentration increases from close to zero in ambient air to about 5 percent in exhaled air. Alternatively, air with a high helium contents, or with anomalous nitrogen contents might be used in the dynamic measurements. Helium is being employed in lung spirometry and for magnetic resonance imaging using hyperpolarized nuclei.

Measurements may also include nitric oxide (NO) in body cavities. Nitric oxide content is often raised during infections and an increased level of NO may be detected by the present invention, concluding a "level of infection", e.g. in the sinuses.

In one embodiment one may use an already known concentration of a substance, such as the water vapour concentration in the lungs or other cavities, only determined by the temperature (37° C.), as a reference to measure an unknown concentration of another substance, such as, in the case of the lungs, the concentration of oxygen or carbon dioxide. This may be achieved since the distance of the traveled light implicitly may be derived from the absorption measurement of the water vapour. Usually, the concentration of water vapour is 100% (=1) in the lungs. This is prerequisite for the correct functioning of the lungs, and among other, gas entering the lungs via the breathing system is humidified to 100% relative humidity (i.e. water vapour content 100%) and heated to body temperature (usually 37° C.) on the way to the lungs;

e.g. the nose is a heat and moisture exchanger ensuring this process. This known concentration may then be used to derive the unknown concentration of the other substance. Hereby, it is possible to measure concentration ratios between different gases to detect physiological anomalies or diseases.

Light for scattering media absorption spectroscopy may be introduced into the body by means of a light guide, e.g. a fiberoptic catheter or endoscope. In this way deeper lying body regions may be analysed for gas containing cavities. For instance, an endoscope may be entered into the oral cavity, the trachea, the oesophagus, the anus etc. Light is thus guided into deeper regions of the body. The scattered light is guided out of the body by the same means to a suitably positioned detector in order to provide a measurement set-up as described above. However, it is envisaged that the main field of application of the invention will be by measuring gas cavities inside the body from the outside of the body, e.g. by placing a measurement head directly onto the skin of a subject. For hygienic purposes, the device may be equipped with single use plastic covers, which might be sterile prior to use, depending on the patient condition and field of application.

Applications and use of the above described device and method according to the invention are various and include exemplary fields such as further diagnostics tasks in medicine. For instance, the lungs are normally surrounded by an air enclosure in the pleural room, which may be displaced by pleural fluid in connection with various illnesses. This condition is hitherto clinically identified by percutation at the chest wall, wherein diagnosis sometimes is not reliable due to human factors, e.g. when done by less experienced medical staff. A much more exact diagnostics is provided by the application of the present technique, e.g. in a backscattering geometry, where areas containing air may be distinguished from those filled with pleural liquid. With the present invention, it is achievable to measure through the chest wall and to reach the pleura for the described measurements.

A further example are measurements through the ear drum for measuring gas content in the inner ear, providing diagnosis of e.g. inflammation of the ear, otitis.

Yet another example are measurements of gases in the gastrointestinal tract of a subject. Both the occurrence and the composition may be detected with the present invention, e.g. enabling detection of certain bacteria or bacterial infections by detecting gas related therewith, e.g. generated by the bacterial infection within the body. Here e.g. *helicobacter pylori* is an example, which generates a detectable gas in the stomach. This may be an alternative to breath tests, where ulcer treatment is based on *helicobacter pylori* detection.

Generally, it is pointed out that the method and device for measuring gas in human cavities is well suited for diagnosis of children and especially well for neonatal subjects. This is due to the fact that the body is smaller than that of grown-up persons, and thus the penetration depth of the light used for gas measurements by light scattering reaches deeper into the body, in relative penetration dimensions.

The invention may be implemented in any suitable form including hardware, software, firmware or any combination of these. The elements and components of an embodiment of the invention may be physically, functionally and logically implemented in any suitable way. Indeed, the functionality may be implemented in a single unit, in a plurality of units or as part of other functional units. As such, the invention may be implemented in a single unit, or may be physically and functionally distributed between different units and processors.

Although the present invention has been described above with reference to specific embodiments, it is not intended to be limited to the specific form set forth herein. Rather, the invention is limited only by the accompanying claims and, other embodiments than the specific above are equally possible within the scope of these appended claims, e.g. different gases to be measured, different wavelengths, light sources, light guides, detectors, etc. than those described above.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A device configured to measure concentration of a free gas in a body cavity, comprising:
    a light emitter arranged to emit an emitted light towards said body cavity from outside said body cavity;
    a light receiver arranged to collect a collected light, said collected light comprising said emitted light that has been scattered from the tissue surrounding said body cavity, a portion of said collected light having passed through said body cavity at least once, wherein said light receiver is configured to observe at least one wavelength window specific for said free gas in the body cavity; and
    a processor configured to assess a concentration of said free gas in said body cavity from said collected scattered light, based on optical absorption spectroscopy;
    wherein said assessing of said concentration of said free gas is a ratio between a measurement signal from said collected light associated with said free gas in said body cavity and a measurement signal from said collected light associated with a known concentration of a reference gas and said reference gas is water vapor.

2. The device according to claim 1 wherein said light receiver is arranged outside the body.

3. The device according to claim 1 wherein said at least one wavelength window specific for a free gas is approximately 1/10000 a wavelength window specific for a substantially identical substance in a nongaseous state.

4. The device according to claim 1 wherein said ratio between measurement signals of said reference gas and said free gas is determinable by said processor as proportional to a concentration of free oxygen or free carbon dioxide.

5. The device of claim 4 wherein said reference gas is water vapor in a lung.

6. The device according to claim 1, wherein said light emitter is comprised in an endoscope or a fiberoptic catheter.

7. The device according to claim 1, in a compact, handheld configuration, adapted to be applied to the outside of said body for measuring said free gas in said body cavity.

8. The device according to claim 1 wherein the light emitter is a near-IR single mode diode laser.

9. The device according to claim 1 wherein the light receiver is a photomultiplier tube.

10. The device according to claim 1 wherein said free gas is selected from the group comprising oxygen, methane, carbon dioxide, water vapour, or nitric oxide.

11. The device according to claim 1, wherein said device is configured to perform said optical absorption spectroscopy in scattering media in transmission or backscattering.

12. The device according to claim 1 wherein said light emitter and said light receiver are arranged in a transmission geometry.

13. The device according to claim 1 wherein said light emitter and said light receiver are arranged in a backscattering geometry.

14. The device according to claim 1 wherein said light receiver is configured to transform said collected scattered light to a signal.

15. The device according to claim 14, comprising a signal splitter for splitting said signal into a first signal and a second signal.

16. The device according to claim 15 wherein said device is configured to send said first signal to a computer controlled digital oscilloscope, and said second signal is sent to a lock-in amplifier.

17. The device according to claim 16 wherein said device is configured to send said second signal thereafter to said oscilloscope.

18. The device according to claim 1 comprising said light emitter and said light receiver in a measurement head directly positionable onto a surface of a human subject.

19. The device according to claim 1, wherein said device is configured to provide dynamic measurements of said free gas.

20. The device according to claim 1 wherein said device is configured for diagnosis of a physiological condition based upon assessment of said concentration of said free gas in said body cavity from said collected scattered light.

21. The device according to claim 20 wherein said physiological condition is respiration of a human subject.

22. The device according to claim 21 wherein said physiological condition comprise inflammations or infections.

23. The device according to claim 22 wherein said free gas is nitric oxide and said device is configured to determine a level of infection from said detected free nitric oxide.

24. The device according to claim 1 wherein said device is configured for diagnosing sinusitis, pleural infections, gastrointestinal diseases, or ear-infections in human subjects.

25. The device according to claim 1, wherein said device is configured for neonatal subjects, having said body cavity.

26. The device of claim 1 wherein said device is configured for diagnosis of a physiological disease process based upon assessment of said concentration of said free gas in said body cavity from said collected scattered light.

27. A method of non-invasively measuring concentration of a free gas in a body cavity, comprising the steps of:
emitting a light towards said body cavity;
collecting said light that has been scattered from tissue surrounding said body cavity, a portion of said light having passed through said body cavity at least once;
observing at least one wavelength window specific for the free gas in the body cavity; and
assessing a concentration of said free gas in said body cavity from said collected scattered light, based on optical absorption spectroscopy;
wherein said concentration of said free gas is assessed by determining a ratio between a measurement signal from said collected light associated with said free gas in said body cavity and a measurement signal from said collected light associated with a known concentration of a reference gas and said reference gas is water vapor.

28. The method of claim 27 wherein said gas is selected from the group consisting of: oxygen, methane, carbon dioxide, water vapour, and nitric oxide.

29. The method according to claim 27 wherein the step of assessing a concentration of said free gas in said body cavity from said collected scattered light, based on optical absorption spectroscopy comprising employing absorption spectroscopy measurement techniques of said gas in scattering media.

30. The method according to claim 27, wherein said measurement is performed in transmission or backscattering.

31. The method according to claim 27 wherein said wavelength window specific for a free gas is approximately 1/10000 of a wavelength window specific for an substantially identical substance in a non-gaseous state.

32. The method according to claim 27 wherein said ratio between measurement signals of said reference gas and said free gas is used to determine a concentration of free oxygen or free carbon dioxide.

33. The method according to claim 32, wherein said concentration of the reference gas is 100% relative humidity and said ratio is directly proportional to said concentration of said free gas.

34. The method of claim 32 wherein said water vapour is the water vapour concentration in a lung.

35. The method according to claim 27, wherein said emitting and collecting is achieved through transmission geometry.

36. The method according to claim 27, wherein said emitting and collecting is achieved through backscattering geometry.

37. The method according to claim 27 further comprising transforming said collected scattered light to a signal.

38. The method according to claim 37 further comprising splitting said signal into a first signal and a second signal.

39. The method according to claim 38 further comprising sending said first signal to a computer controlled digital oscilloscope and sending said second signal to a lock-in amplifier.

40. The method according to claim 39 further comprising sending said second signal thereafter to said oscilloscope.

41. The method according to claim 27 wherein the step of emitting a light towards said body cavity comprises introducing light into a human body by a light guide for analysing body regions for free gas containing cavities.

42. The method of claim 41 wherein said light guide comprises a fiberoptic catheter.

43. The method of claim 41 wherein said light guide comprises an endoscope.

44. The method of claim 41 wherein said light guide comprises a fiberoptic catheter.

45. The method according to claim 27 wherein the step of emitting a light towards said body cavity comprises introducing light from the outside of the human body.

46. The method according to claim 45 further comprising placing a measurement head directly onto an external surface of a human subject.

47. The method of claim 46 wherein said human subject is a neonatal human subject.

48. The method according to claim 27 wherein the step of assessing a concentration of said free gas in said body cavity from said collected scattered light, based on optical absorption spectroscopy comprises assessing dynamically the concentration of said free gas in said body cavity.

49. The method of claim 27 further comprising the step of detecting a physiological condition based upon said step of assessing a concentration of said free gas in said body cavity from said collected scattered light.

50. The method of claim 49 wherein said physiological condition comprises respiration of a human subject.

51. The method of claim 49 wherein said physiological condition comprises inflammations or infections.

52. The method of claim 51 wherein said free gas is nitric oxide and a level of detected free nitric oxide is used to determine a level of infection.

53. The method of claim 49 wherein said physiological condition is a condition selected from a group of conditions consisting of: sinusitis, pleural infections, gastro-intestinal diseases, and ear-infections.

54. The method of claim 27 further comprising the step of detecting a disease process based upon said step of assessing a concentration of said free gas in said body cavity from said collected scattered light.

* * * * *